(12) United States Patent
Cao et al.

(10) Patent No.: US 10,925,912 B2
(45) Date of Patent: Feb. 23, 2021

(54) PREPARATION AND APPLICATION OF GINSENG DERIVED MEMBRANOUS MICROPARTICLES

(71) Applicant: JIANGSU PROVINCE INSTITUTE OF TRADITIONAL CHINESE MEDICINE, Nanjing (CN)

(72) Inventors: Peng Cao, Nanjing (CN); Meng Cao, Nanjing (CN); Huaijiang Yan, Nanjing (CN)

(73) Assignee: JIANGSU PROVINCE INSTITUTE OF TRADITIONAL CHINESE MEDICINE, Nanjing (CN)

(*) Notice: Subject to any disclaimer, the term of this patent is extended or adjusted under 35 U.S.C. 154(b) by 0 days.

(21) Appl. No.: 16/483,021

(22) PCT Filed: Jun. 19, 2017

(86) PCT No.: PCT/CN2017/088953
§ 371 (c)(1),
(2) Date: Aug. 1, 2019

(87) PCT Pub. No.: WO2018/152989
PCT Pub. Date: Aug. 30, 2018

(65) Prior Publication Data
US 2020/0016223 A1 Jan. 16, 2020

(30) Foreign Application Priority Data

Feb. 22, 2017 (CN) .......................... 201710094457.7
Apr. 17, 2017 (CN) .......................... 201710248242.6

(51) Int. Cl.
| | |
|---|---|
| *A61K 36/258* | (2006.01) |
| *A61P 37/04* | (2006.01) |
| *A61P 31/18* | (2006.01) |
| *A61P 25/00* | (2006.01) |
| *A61P 31/06* | (2006.01) |
| *A61P 35/00* | (2006.01) |
| *A61K 9/14* | (2006.01) |

(52) U.S. Cl.
CPC .............. *A61K 36/258* (2013.01); *A61K 9/14* (2013.01); *A61P 25/00* (2018.01); *A61P 31/06* (2018.01); *A61P 31/18* (2018.01); *A61P 35/00* (2018.01); *A61P 37/04* (2018.01)

(58) Field of Classification Search
None
See application file for complete search history.

(56) References Cited

U.S. PATENT DOCUMENTS

2019/0125690 A1* 5/2019 Yang .................... A61K 9/5192

FOREIGN PATENT DOCUMENTS

| CN | 1883556 | * | 12/2006 |
| CN | 102949421 A | * | 3/2013 |
| CN | 105708847 | * | 6/2016 |

OTHER PUBLICATIONS

Verma M. et al. Novel Drug Delivery System for Cancer Management. Current Cancer Therapy Reviews 12(4)253-272, Dec. 2016. (Year: 2016).*
Cao M. et al. Ginseng Derived Nanoparticles Alter Macrophage Polarization to Inhibit Melanoma Growth. J for Immunotherapy of Cancer 7(1)1-18, Nov. 2019. (Year: 2019).*
Liu, Xi-Hua et al. Progress in Novel Drug Delivery System of Anti-Tumor Medicine Ginsenosides. Zhongguo Shiyan Fangixue Zazhi 21(9)231-234, 2015. (Year: 2015).*
Kang, S. et al. Ginseng, The Immunity Boost. J of Ginseng Research 36(4)354-368, 2012. (Year: 2012).*

* cited by examiner

*Primary Examiner* — Ralph J Gitomer
(74) *Attorney, Agent, or Firm* — CBM Patent Consulting, LLC

(57) ABSTRACT

The invention discloses a ginseng-derived nanoparticle and a preparation method and application thereof. The ginseng-derived nanoparticle disclosed in the invention has a membrane structure, a particle size ranging from 150 to 500 nm and a peak particle size of 280 to 350 nm; and the ginseng-derived nanoparticle is prepared by multiple centrifugation, filtration and impurity removal. The ginseng-derived nanoparticle has good application prospects in developing drugs for preparing natural immunopotentiators and for preparing natural anti-tumor drugs.

7 Claims, 10 Drawing Sheets

2-1

2-2

2-3

Control group　　　　　　　　　　　　　　With GDNPs

Leukocyte differentiation antigen 86

Leukocyte differentiation antigen 80

Leukocyte differentiation antigen 40

Major histocompatibility complex 2

Toll-like receptor 2

Toll-like receptor 4

Control group    With GDNPs

PREPARATION AND APPLICATION OF GINSENG DERIVED MEMBRANOUS MICROPARTICLES

TECHNICAL FIELD

The invention belongs to the field of immunopotentiators, and in particular relates to a ginseng-derived microparticle and preparation and application thereof.

BACKGROUND ART

Microvesicles are one type of extracellular vesicles. Unlike exosomes, microvesicles are mainly nanoscale particles with a diameter of about 100 to 1000 nm produced by outward germination of the plasma membrane. These microparticles often carry a variety of active substances such as proteins, DNA, RNA, etc., and have various biological activities.

An immunopotentiator generally refers to a substance that may enhance the immune response of organism when used alone or in combination with an antigen, and is also referred to as an immunomodulator or an immunostimulant. The immunopotentiator can act through different pathways, such as enhancing the activity of monocyte-macrophages, enhancing the immunogenicity and stability of antigenic substances, and promoting the synthesis and secretion of antibodies, so as to enhance the specific and non-specific immune response of the organism.

Monocyte-macrophages are phagocytic cells commonly found in blood, lymph, and all mammalian tissue types. Monocyte-macrophages are the most plastic cells in the hematopoietic system, exist in all tissues, and have a strong functional diversity. Their main function is to eliminate aging cells, tumor cells and pathogens in the form of fixed cells or free cells, and activate other immune cells; and to play many different roles in normal development, homeostasis, tissue repair, and immune response to pathogens.

Since monocyte-macrophages play an important role in the organism's non-specific immune response and specific immune response, and are widely distributed in the body, how to regulate the activity of monocyte-macrophages is one of research hotspot in immunology. Traditional granulocyte-macrophage colony-stimulating factor can only promote the growth of monocyte-macrophages, and cannot activate TLR and other related immune molecules, thus cannot fully promote the cell-mediated immune response so that pathogens and tumor cell components located in the cells cannot be removed. Due to mild drug properties, low drug resistance, small toxic and side effects, and the characteristics of two-way adjustment function, a traditional Chinese medicine immunopotentiator has become a research hotspot of immunopotentiators.

Tumor microenvironment refers to a local steady state environment composed of tumor cells, stromal cells (including fibroblasts, immune and inflammatory cells, adipocytes, glial cells, smooth muscle cells, and some vascular endothelial cells, etc.) and extracellular matrix during tumor growth, providing necessary material basis for occurrence, development, invasion and metastasis and the like of tumors. The tumor microenvironment has an important support and promotion effect on tumors. How to intervene and improve the tumor microenvironment is a core issue to prevent tumor development and metastasis.

Recent studies have shown that tumor-associated macrophages (TAM), which are grown in the tumor microenvironment, are important components of the tumor microenvironment and play a key role in each stage of tumor development and metastasis.

Macrophage (Mq) is one of the important immune cells of organism and plays an important role in the host's immune defense and maintenance of tissue homeostasis. According to functional characteristics, macrophages are mainly activated into two subtypes: classically activated macrophage (M1 type) and alternatively activated macrophage (M2 type). M1 type is regulated by cytokines secreted by Th1, such as interferon-γ (INF-γ), lipopolysaccharide (LPS) and Toll-like receptor (TLR), and is characterized by secretion of pro-inflammatory factors including IL-6, IL-12, IL-23, tumor necrosis factor-α (TNF-α), etc. In addition, M1 type macrophages also highly express major histocompatibility complex class I and class II molecules for efficient antigen presentation. Therefore, M1 type macrophages are considered to be cells that kill bacteria and tumor cells and secrete various pro-inflammatory cytokines. M2 type macrophages, in contrast to the M1 type, are recognized as cells that promote tumor growth, invasion, and metastasis. The vast majority of TAM belong to M2 type macrophages, which are the most important tumor infiltrating leukocytes in humans and mice. In the early stage of tumor invasion and metastasis, tumor cells release chemokines to recruit macrophages and other inflammatory cells to reach the stromal area around the tumor, and then TAM can penetrate the basement membrane to allow the tumor cells to escape from the binding of the basement membrane to the surrounding normal tissue matrix, while both TAM and tumor cells stimulate angiogenesis and increase cell invasiveness and motility[11]. TAM also promotes angiogenesis by releasing angiogenic regulatory enzymes such as matrix metalloprotein 2 (MMP2), MMP-9, MMP-12, and cyclooxygenase 2 (COX2) to deliver nutrients for tumor growth. In addition, TAM can also release a series of cytokines and growth factors that promote tumor cell infiltration and metastasis, such as vascular endothelial growth factor (VEGF), basic fibroblast growth factor (bEGF), etc.

Based on the important role of TAM in the tumor microenvironment, how to exert the heterogeneity and plasticity of macrophages, and promote the polarization of TAM to M1 to improve the tumor microenvironment may become an important target for tumor immunotherapy.

Ginseng is one of the most important Chinese herbal medicines in China. It is known as the "King of Herbs" and has a very high medicinal value. The microparticle-sized microvesicles produced by ginseng carry a variety of active ingredients of ginseng, which may be one of the important ways for exerting their effects.

SUMMARY OF THE INVENTION

The technical problem to be solved by the present invention is to provide a ginseng-derived microparticle (GDMP for short) which can achieve scale production, and use of the same as a natural immunopotentiator and in preparation of a drug for treating tumors. Microvesicles of the ginseng-derived microparticle contain a variety of bioactive components of ginseng, and thus have a good application prospect as a novel natural immunopotentiator.

In order to solve the above technical problems, the technical solution adopted by the present invention is as follows:

Provided is a ginseng-derived microparticle having a membrane structure, a particle size ranging from 150 to 500 nm and a peak particle size of 280 to 350 nm.

The preparation method of the ginseng-derived microparticles comprises the following steps:

(1) squeezing fresh and washed ginseng by a low-speed screw extrusion technology to obtain a slurry;

(2) filtering the slurry obtained in step (1) through a sieve to remove impurities and collecting a filtrate;

(3) sequentially subjecting the filtrate obtained in step (2) to low-speed, medium-speed, high-speed and ultra-speed centrifugation, discarding a precipitate after each centrifugation, and collecting a supernatant for the next centrifugation, wherein the precipitate is collected after the last centrifugation;

(4) resuspending the precipitate collected by the last centrifugation in step (3) with a buffer, then subjecting a mixture to ultra-speed centrifugation once, and collecting a precipitate; resuspending the precipitate with a buffer again, then subjecting a mixture to high-speed centrifugation and collecting a supernatant; passing the supernatant through a sterilizing grade filter membrane to obtain the ginseng-derived microparticle.

Preferably, the above operation is carried out in an environment of 4 to 25° C.

In step (1), the rotation speed of the low-speed screw extrusion is 30 to 60 rpm.

In step (2), the sieve has 200 to 2,000 meshes, preferably 200 to 1,000 meshes.

In step (3), for the low-speed centrifugation, the centrifugal force is 100 to 500×g, and the centrifugation time is 5 to 10 minutes; for the medium-speed centrifugation, the centrifugal force is 1,000 to 5,000×g, and the centrifugation time is 10 to 30 minutes; for the high-speed centrifugation, the centrifugal force is 8,000 to 12,000×g, and the centrifugation time is 30 to 60 minutes; for the ultra-speed centrifugation, the centrifugal force is 100,000 to 200,000×g, and the centrifugation time is 60 to 120 minutes, the number of each of the low-speed, medium-speed, high-speed and ultra-speed centrifugation is at least one.

Preferably, the centrifugal force of the low-speed centrifugation is 200 to 500×g; the centrifugal force of the medium-speed centrifugation is 2,000 to 5,000×g; the centrifugal force of the high-speed centrifugation is 100,000 to 12,000×g; the centrifugal force of the ultra-speed centrifugation is 100,000 to 120,000×g.

In step (4), the buffer is a phosphate buffer, the pH of the buffer is pH 7.2 to 7.4; for the ultra-speed centrifugation, the centrifugal force is 100,000 to 200,000×g, and the centrifugation time is 60 to 120 minutes; for the high-speed centrifugation, the centrifugal force is 8,000 to 12,000×g, and the centrifugation time is 30 to 60 minutes; the pore size of the sterilizing grade filter membrane is 0.45 μm.

Provided is the use of ginseng-derived microparticle for treating diseases caused by various low immune functions such as AIDS, active tuberculosis, oral *Candida albicans* infection, toxoplasma encephalopathy, Kaposi sarcoma and the like.

Provided is the use of the ginseng-derived microparticle in preparation of a drug as an immunopotentiator for activating monocyte-macrophages.

The method for activating monocyte-macrophages is promoting proliferation of monocyte-macrophages and formation of colonies or up-regulating immunologically active molecules on the surface of the monocyte-macrophages or promoting immunologically active cytokines secreted by the monocyte-macrophages.

The immunologically active molecule is one or more of Toll-like receptor 2/4 (TLR2/4), leukocyte differentiation antigen 80 (CD80), leukocyte differentiation antigen 86 (CD86), major histocompatibility complex 2 (MHC-II); the immunologically active cytokine is one or more of tumor necrosis factor-α (TNF-α) and interleukin-6 (IL-6).

Provided is the use of the ginseng-derived microparticle in preparation of a drug for treating tumors.

The method for treating a tumor is re-polarizing tumor-associated macrophages.

The method for re-polarizing tumor-associated macrophages is: down-regulating surface marker molecules of M2 type macrophages, up-regulating surface marker molecules of M1 type macrophages, up-regulating cytokines secreted by the M1 type macrophages, and changing the proportion of the M1/M2 type macrophages in the tumor microenvironment, so as to improve the tumor microenvironment and kill tumors.

The M2 type macrophage-associated surface marker molecule is leukocyte differentiation antigen 206 (CD206); the M1 type macrophage-associated surface marker molecule is one or more of Toll-like receptor 2/4 (TLR2/4), leukocyte differentiation antigen 80 (CD80), leukocyte differentiation antigen 86 (CD86), and major histocompatibility complex 2 (MHC-II); the M2 type macrophage-associated gene is one or more of arginase 1 (Arg-1), leukocyte differentiation antigen 206, also known as macrophage mannose receptor (CD206), interleukin-10 (IL-10), and chitinase 3-like molecule (CHI313); the M1 type macrophage-associated gene is one or more of interleukin-6 (IL-6), tumor necrosis factor-α (TNF-α), leukocyte differentiation antigen 80 (CD80), chemokine 9 (CXCL9), chemokine 3 (CCL3), inducible nitric oxide synthase (iNOS) and the like; the M1 type macrophage-associated immunologically active cytokine is one or more of tumor necrosis factor-α (TNF-α) and interleukin-6 (IL-6).

Provided is a pharmaceutical composition comprising the ginseng-derived microparticle.

Provided is a pharmaceutical formulation comprising a therapeutically effective amount of the ginseng-derived microparticles or a pharmaceutically acceptable excipient of the pharmaceutical composition.

The ginseng-derived microparticle material according to the invention has wide sources, which can be ginseng, American ginseng, Notoginseng, *Codonopsis pilosula, Pseudostellaria heterophylla, Salvia miltiorrhiza*, and *Scrophularia ningpoensis*; the preparation method according to the invention has the advantages of easy operation, less time consumption and the like.

Advantageous Effects: The ginseng-derived microparticle according to the present invention can effectively induce proliferation and activation of bone marrow-derived monocyte-macrophages, simultaneously up-regulate TLR2/4, CD80, and other surface active molecules, and secrete TNF-α, IL-6 and other cytokines, thus having a good application prospect in the development of a drug for preparing a natural immunopotentiator; the use of the ginseng-derived microparticle according to the invention in preparation of a drug for treating tumors can effectively polarize tumor-associated macrophages from M2 type that promotes tumor growth to anti-tumor M1 type, simultaneously up-regulate M1 type-associated TLR2/4, CD80 and other surface active molecules, and secrete TNF-α, IL-6 and other cytokines, so as to improve the tumor microenvironment, thus having a good application prospect in the development of natural anti-tumor drugs.

BRIEF DESCRIPTION OF THE DRAWINGS

FIGS. 2-1, 2-2 and 2-3 show the particle size and distribution of ginseng-derived, American ginseng-derived and Notoginseng-derived microparticles, respectively;

FIG. 3 shows the uptake of GDMPs by monocyte-macrophages;

DETAILED DESCRIPTION OF THE INVENTION

Figure 1:
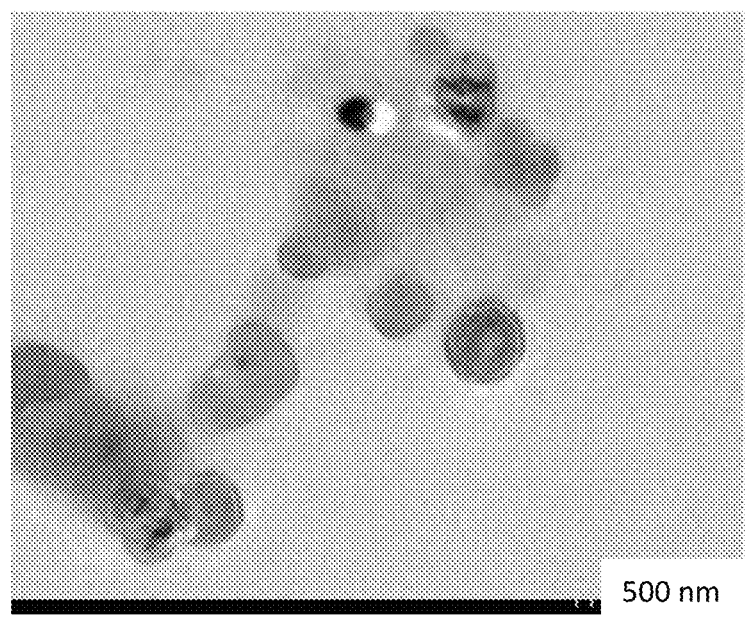
FIG. 1 shows the morphology of GDMPs observed by electron microscopy.

The invention can be better understood in light of the following examples. However, those skilled in the art will understand that the description of the examples is only intended to illustrate the invention, should not and would not be construed as limiting the invention as described in the claims.

Example 1: Preparation of Ginseng-Derived Microparticles (1) The fresh ginseng was washed with clear water and squeezed by a low-speed screw extrusion technology in an environment of 20° C. to obtain a slurry;

(2) The squeezed slurry was filtered through a 500 mesh sieve in an environment of 20° C. to remove impurities, and a filtrate was collected;

(3) The collected filtrate was centrifuged at 200×g for 10 minutes, a precipitate was discarded, and a supernatant was collected; the supernatant was centrifuged at 2,000×g for 30 minutes, a precipitate was discarded, and a supernatant was collected; the supernatant was centrifuged at 10,000×g for 60 minutes, a precipitate was discarded, and a supernatant was collected; finally, the supernatant was centrifuged at 120,000×g for 60 minutes, and a precipitate was collected;

(4) The precipitate was resuspended in a phosphate buffer at pH 7.2, and then centrifuged at 120,000×g for 60 minutes, and a precipitate was collected; the precipitate was resuspended in the phosphate buffer at pH 7.2 again, and then centrifuged at 10,000×g for 60 minutes, and a supernatant was collected; finally, the supernatant was passed through a sterilizing grade filter membrane with a pore size of 0.45 μm to obtain the nanoscale particle. The microparticles were stored at −20° C. to −80° C.

Example 2: Preparation of American Ginseng-Derived Microparticles (1) The fresh American ginseng was washed with clear water and squeezed by a low-speed screw extrusion technology in an environment of 10° C. to obtain a slurry;

(2) The squeezed slurry was filtered through a 200 mesh sieve in an environment of 10° C. to remove impurities, and a filtrate was collected;

(3) The collected filtrate was centrifuged at 500×g for 5 minutes, a precipitate was discarded, and a supernatant was collected; the supernatant was centrifuged at 5,000×g for 10 minutes, a precipitate was discarded, and a supernatant was collected; the supernatant was centrifuged at 12,000×g for 30 minutes, a precipitate was discarded, and a supernatant was collected; finally, the supernatant was centrifuged at 100,000×g for 90 minutes, and a precipitate was collected;

(4) The precipitate was resuspended in a phosphate buffer at pH 7.4, and then centrifuged at 100,000×g for 90 minutes, and a precipitate was collected; the precipitate was resuspended in the phosphate buffer at pH 7.4 again, and then centrifuged at 12,000×g for 30 minutes, and a supernatant was collected; finally, the supernatant was passed through a sterilizing grade filter membrane with a pore size of 0.45 μm to obtain the nanoscale particles. The microparticles were stored at −20° C. to −80° C.

Example 3: Preparation of Notoginseng-Derived Microparticles (1) The fresh Notoginseng was washed with clear water and squeezed by a low-speed screw extrusion technology in an environment of 25° C. to obtain a slurry;

(2) The squeezed slurry was filtered through a 1,000 mesh sieve in an environment of 25° C. to remove impurities, and a filtrate was collected;

(3) The collected filtrate was centrifuged at 500×g for 10 minutes, a precipitate was discarded, and a supernatant was collected; the supernatant was centrifuged at 5,000×g for 30 minutes, a precipitate was discarded, and a supernatant was collected; the supernatant was centrifuged at 12,000×g for 45 minutes, a precipitate was discarded, and a supernatant was collected; finally, the supernatant was centrifuged at 200,000×g for 60 minutes, and a precipitate was collected;

(4) The precipitate was resuspended in a phosphate buffer at pH 7.3, and then centrifuged at 200,000×g for 60 minutes, and a precipitate was collected; the precipitate was resuspended in the phosphate buffer at pH 7.3 again, and then centrifuged at 12,000×g for 45 minutes, and a supernatant was collected; finally, the supernatant was passed through a sterilizing grade filter membrane with a pore size of 0.45 μm to obtain the nanoscale particle. The microparticles were stored at −20° C. to −80° C.

Example 4: Observation on Morphology of GDMPs by Electron Microscopy

The extracted GDMPs were subjected to ultra-speed centrifugation at 120,000×g for 60 minutes, and then the GDMPs were precipitated and compacted. A supernatant was discarded. A precipitate was fixed with 2.5% (v/v) glutaraldehyde, and processed in an electron microscopy room. The morphology of GDNPs was observed under the microscope. As shown in FIG. 1, under the electron microscope, it can be seen that GDNPs were microparticles having a membrane structure and a size ranging from 150 to 500 nm, which confirms the effective recruitment of ginseng-derived nanoscale microbodies.

Figure 2:
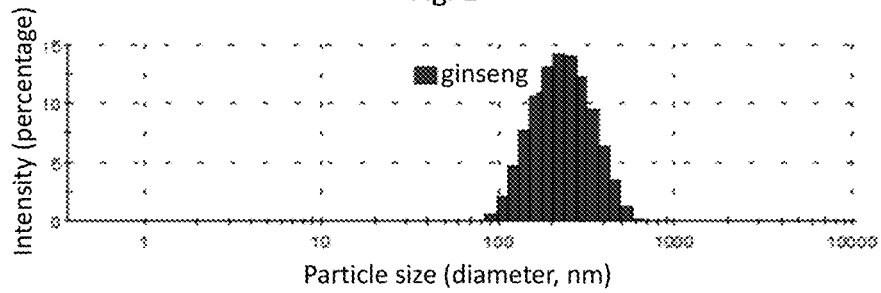
FIG. 2 shows the particle size of GDMPs analyzed by Malvern particle size analyzer.
Figure 2:
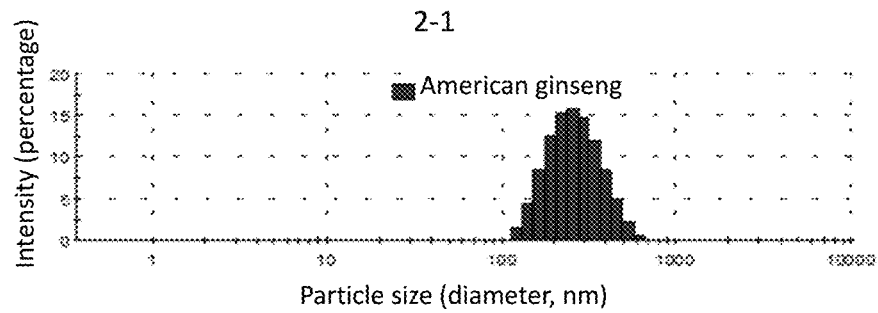
Figure 2:
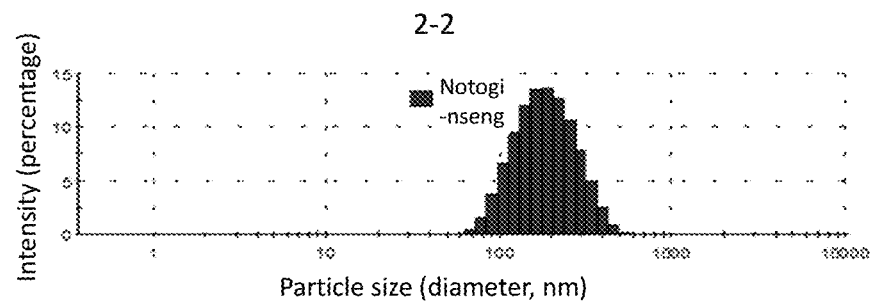
Figure 3:
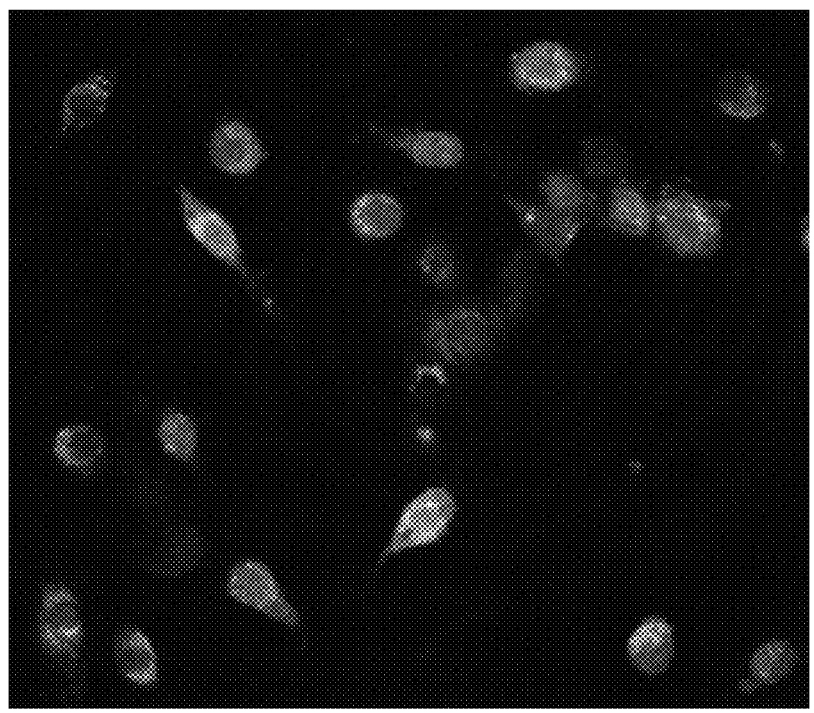

Example 5: Detection of the Particle Size of Plant-Derived Microparticles by Malvern Particle Size Analyzer The extracted GDMPs were detected by a Malvern particle size analyzer for particle size. FIGS. 2-1, 2-2, and 2-3 show the particle size and distribution of ginseng-derived, American ginseng-derived and Notoginseng-derived microparticles, respectively. Also, the peak homogeneity of the extracted GDMPs is better.

Example 6: GDMPs Promote Formation and Proliferation of Monocyte-Macrophage Colonies In Vitro 1. Acquisition of Bone Marrow-Derived Monocyte-Macrophages (BMDM)
  a. C57/BL6 mice were sacrificed by cervical dislocation and soaked in alcohol for 5 minutes. After fixing the mice, the fur of the anterior part of the hind limb of the mice was peeled to the foot, the muscle was bluntly separated, and the thigh was cut and placed in a culture dish containing sterile PBS.
  b. The shank was gripped with forceps, the remaining muscles were removed with scissors, and the shank was cut at the joints.
  c. the PBS in the culture dish was pipetted with a 1 mL syringe, the needle head was punctured into the marrow cavity, the bone marrow was rinsed repeatedly until the bone marrow turned white, and the rinsing solution of bone marrow was filtered through a sieve.
  d. The mouse bone marrow was taken, the red blood cells were lysed, and the cell concentration was adjusted to $1*10^6$ cells/ml. A medium was DMEM (Gibco)+10% FBS (Gibco)+20 ng/ml M-CSF (Peprotech).
  e. Bone marrow was taken on day 0, and 10 ml of complete medium containing 20 ng/ml M-CSF was added to each dish on day 3.
  f. After 5 days, 20 ng/ml M-CSF was added to each dish.
  g. After 7 days, BMDM was trypsinized and added to a 6-well cell culture plate with $2*10^6$ cells per well, and 1 ml or 2 ml of medium was added.
2. Uptake of GDMPs by BMDM
  a. BMDM was stained by FITC-labeled Anti-mouse F4/80 antibody on the previous day and added to a culture dish with a slide for adherent growth.
  b. 100 ul of GDMPs was diluted to 250 ul with a dilution.
  c. 1 ul of PKH26 was added to 250 ul of dilution to serve as a dye.
  e. The diluted GDNPs was added to the dye and mixed quickly.
  f. The mixture was incubated at 25° C. for 2 to 5 minutes, a centrifuge tube was gently inverted at regular intervals to ensure a thorough mixing at 25° C.
  g. The same amount of serum was added to stop the staining reaction and incubation was performed for 1 minute.
  h. An ultra-speed centrifugation was performed at 120000×g for 60 minutes.
  i. A supernatant was aspirated and discarded and the stained GDMPs was resuspended in 100 ul PBS.
  j. The GDNPs were added to the cultured BMDM at a concentration of 20 ug/ml and cultured for 24 hours.
  k. The slide was removed and the phagocytosis of GDMPs by monocyte-macrophages was observed with laser confocal microscopy.

As shown in FIG. 3. F4/80 is a specific surface marker molecule of monocyte-macrophages in mice. The mouse BMDM had green fluorescence by FITC-labeled Anti-mouse F4/80 antibody. PKH26 is a red film dye that can bind to a film on the surface of GDMPs. Under laser confocal microscopy, it was observed that multiple red particles appeared in the monocyte-macrophages, indicating that monocyte-macrophages can effectively phagocytose GDMPs.

3. Induction of Formation and Proliferation of Monocyte-Macrophage Colony by GDMPs In Vitro
  a. The induced BMDM was adjusted to a cell concentration of $5*10^5$ cells/ml and added to a 96-well cell culture plate at 100 ul per well.
  b. GDMPs were added to each well at a final concentration of 20 ug/ml.
  c. Formation of monocyte-macrophage colonies was observed under microscopy after 72 hours.
  d. Cell proliferation was detected by MTT assay.

Figure 4:
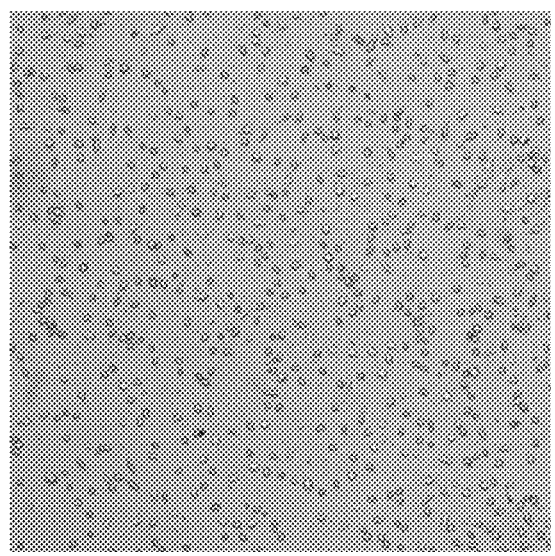
FIG. 4 shows the formation of monocyte-macrophage colonies induced by GDMPs in vitro.
Figure 4:
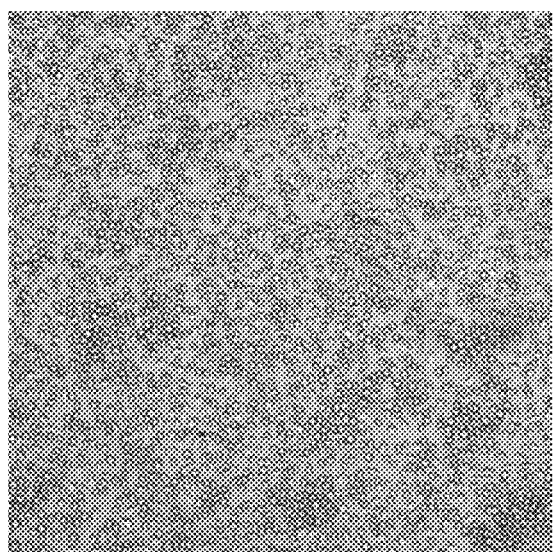
Figure 5:
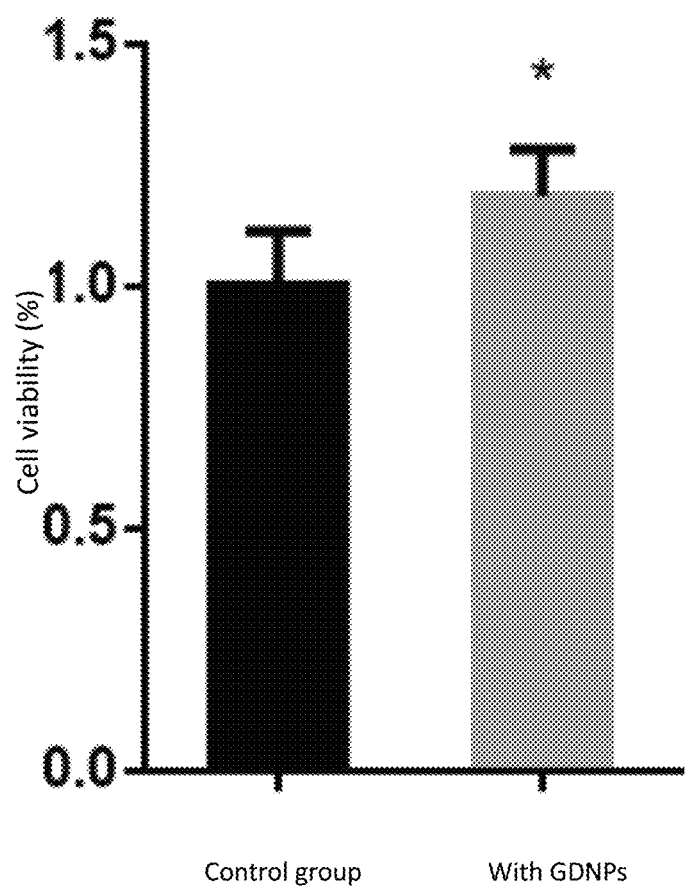
FIG. 5 shows that GDMPs induce the proliferation of monocyte-macrophage in vitro.

As shown in FIG. 4, the left panel shows the BMDM cultured with the same volume of PBS for 72 hours. The right panel shows the BMDM cultured with GDMPs (20 ug/ml) for 72 hours. It can be observed that after adding the GDMPs, the proliferation of the monocyte-macrophages was evident and clone cell colonies were appeared. As shown in FIG. 4. MTT assay shows that GDMPs could significantly stimulate the proliferation of BMDM. After adding the GDMPs, the activity of monocyte-macrophages was significantly higher than that of the control group.

Example 7: GDMPs Up-Regulate CD86, CD80, TLR2/4 and Other Immunologically Active Molecules on the Surface of Monocyte-Macrophages GDMPs were added to mouse BMDM induced in vitro, and a supernatant was aspirated after 72 hours.

1. Up-Regulation of Expression of Associated Activating Molecules on the Surface of Monocyte-Macrophages by GDMPs
  a. BMDM in C57/BL6 mice was obtained by induction, and monocyte-macrophages were stimulated with 20 ug/ml GDMPs.
  b. After 72 hours, the culture supernatant was aspirated, and the cells were trypsinized after washing with PBS once.
  c. A culture solution was added to terminate the digestion, and monocyte-macrophages were collected by centrifugation at 1200 rpm and blocked with an Fc blocking agent (room temperature, 20 minutes).
  d. Anti-mouse CD80, CD86, TLR2, TLR4, MHC-II and other monoclonal antibodies were added respectively (room temperature, 30 minutes), and washed with PBS twice. The expression of the above molecules was identified by flow cytometry.

Figure 6:
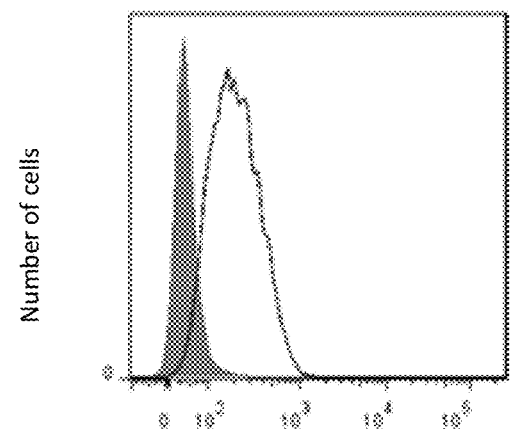
FIG. 6 shows that GDMPs up-regulate a variety of immunologically active molecules on the surface of monocyte-macrophages.
Figure 6:
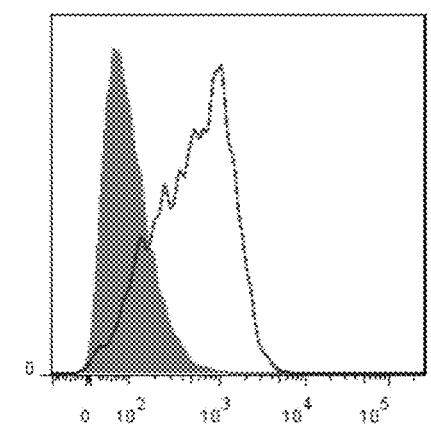
Figure 6:
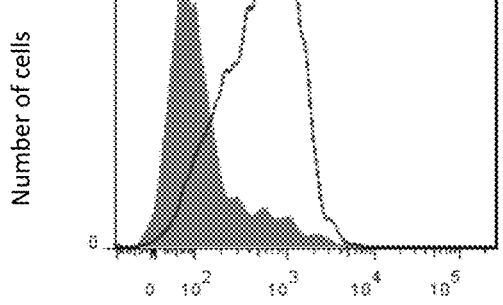
Figure 6:
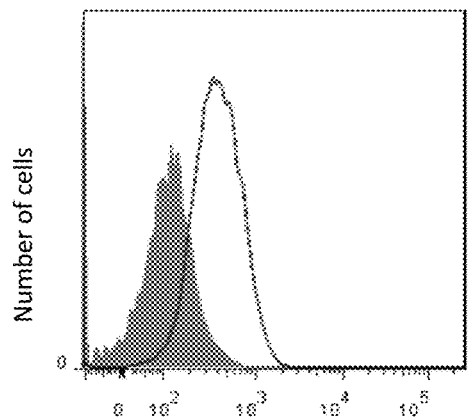
Figure 6:
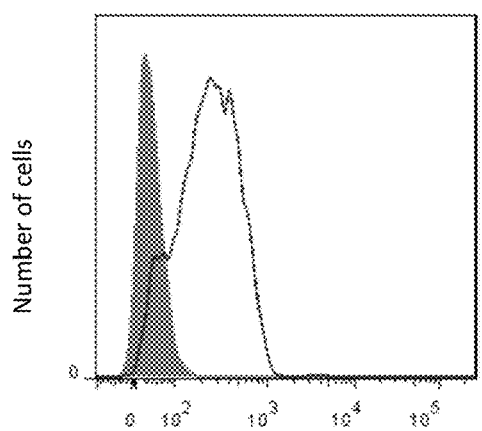
Figure 6:
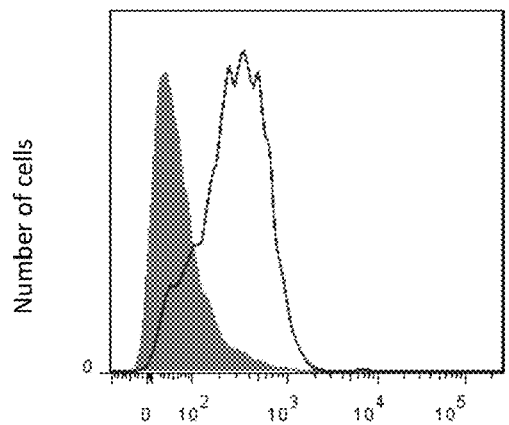
Figure 6:
Figure 6:

As shown in FIG. 6, GDMPs can significantly up-regulate a variety of activating molecules (CD80, CD86, TLR2, TLR4, MHC-II, etc.) on the surface of monocyte-macrophages to activate monocyte-macrophages.

Example 8: GDMPs Promote Secretion of TNF-α, IL-6 and Other Cytokines from Monocyte-Macrophages 1. Detection of TNF-α and IL-6 in the culture supernatant of Example 3 (ELISA method)

a. The capture antibody (anti-mouse TNF-α or IL-6) was diluted as required by the instructions, and coated in a 96-well plate at 100 ul/well at 4° C. overnight.

b. The plate was washed 3 times with PBST (PBS containing 0.5% Tween) for 3 minutes each time, and was then blocked with a 2% sheep serum blocking solution at 37° C. for 2 hours.

c. The plate was washed 3 times with PBST. A culture supernatant sample and a standard dilution were sequentially added to the blocked 96-well plate and incubated at 37° C. for 1 hour.

d. The plate was washed 5 times with PBST, and HRP-antimouse-TNF-α or IL-6 (1:10000) was added, and incubated at 37° C. for 1 hour.

e. The plate was washed 5 times with PBST, and a TMB coloring solution was added, and incubated at 37° C. for 15 minutes.

f. An $H_2SO_4$ stop solution was added and the OD value was measured at 450 nm.

g. The concentration of TNF-α or IL-6 was calculated based on the OD value.

Figure 7:
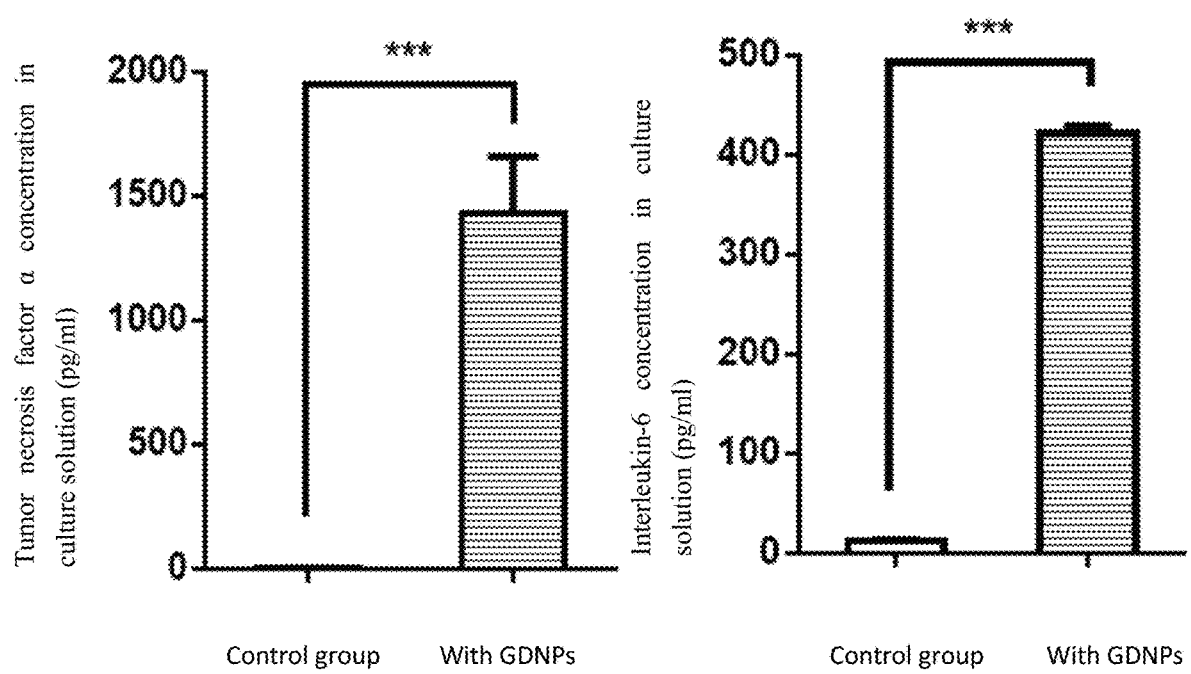
FIG. 7 shows that GDMPs stimulate the secretion of monocyte-macrophage activation-associated cytokines.

As shown in FIG. 7. GDMPs can significantly stimulate monocyte-macrophages to secrete monocyte-macrophage activation-associated cytokines (TNF-α and IL-6).

Example 9: GDMPs Down-Regulate M2 Type Macrophage Surface Marker Molecules while Up-Regulating M1 Type-Associated Surface Marker Molecules a. BMDM in C57/BL6 mice was induced by M-CSF (20 ng/ml), and differentiated into M2 type macrophages by adding IL-4 (20 ng/ml) and IL-13 (20 ng/ml).

b. GDMPs (20 ug/ml) were added, after 72 hours, a culture supernatant was aspirated, and the cells were trypsinized after washing once with PBS.

c. A culture solution was added to terminate the digestion, the macrophages were collected by centrifugation at 1200 rpm and blocked with an Fc blocking agent (room temperature, 20 minutes).

d. Anti-mouse CD206, CD80, CD86, TLR2, TLR4, MHC-II and other monoclonal antibodies were added (room temperature, 30 minutes), and washed twice with PBS. The expression of the above molecules was identified by flow cytometry.

Figure 8:
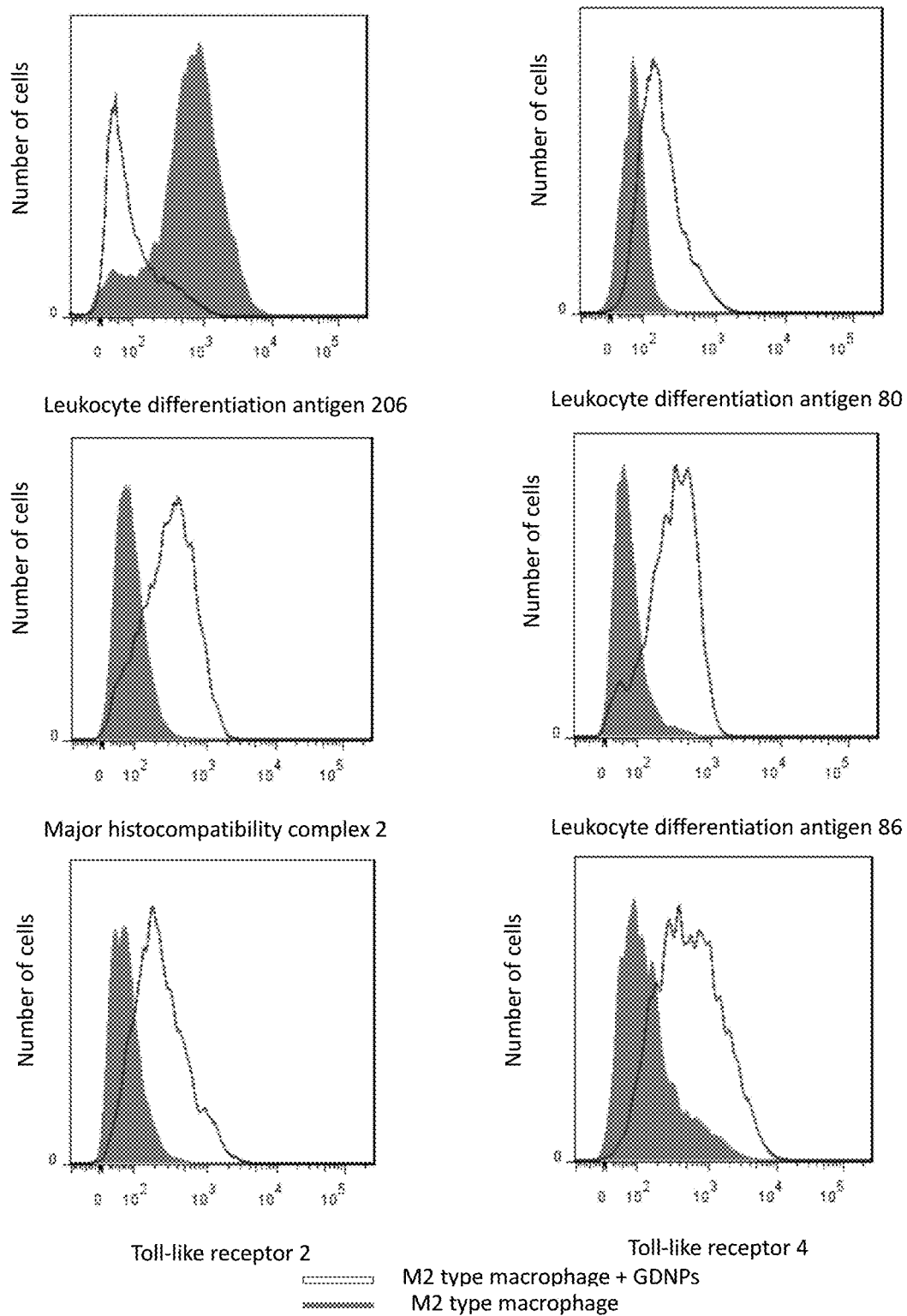
FIG. 8 shows that GDMPs down-regulate M2 type macrophage-associated surface marker molecules in vitro, while up-regulating M1 type-associated surface marker molecules.

As shown in FIG. 8, GDMPs can significantly down-regulate the surface marker molecules (CD206) of M2 type macrophages, while up-regulating the surface marker molecules (CD80, CD86, TLR2, TLR4, MHC-II, etc.) of M1 type macrophages. From the results of surface molecular markers, it is confirmed that GDMPs can polarize M2 type macrophages to M1 type.

Example 10: GDMPs Down-Regulate Transcription of M2 Type Macrophage-Associated Genes In Vitro, while Up-Regulating Transcription of M1 Type-Associated Genes 1. Extraction of Total RNA from Macrophages a. 1 ml of Trizol was added to part of the cells in Example 1, aspirated into an 1.5 ml EP tube, blown until the liquid was clear and free of cell mass, mixed upside down 10 times, and allowed to stand at room temperature for 5 minutes.

b. 200 ul of chloroform was added, shaken vigorously for 15 seconds for RNA extraction and allowed to stand at room temperature for 3 minutes.

c. Centrifugation was performed at 4° C. and 12000 RPM for 15 minutes.

d. An upper aqueous phase was pipetted into a new 1.5 ml EP tube, an equal volume of isopropanol was added, mixed upside down, and allowed to stand at room temperature for 10 minutes.

e. Centrifugation was performed at 4° C. and 12000 RPM for 10 minutes.

f. A supernatant was discarded, pre-cooled 0.5 ml of 75% ethanol (DEPC-Treated Water) was added, the precipitate was washed, mixed, and centrifuged at 4° C. and 7500 RPM for 5 minutes.

g. A supernatant was discarded and dried at room temperature for 5 to 10 minutes.

h. 20 to 60 ul of deionized water was added to dissolve the RNA, blowing and uniform mixing were performed, and placement is performed in a water bath at 56° C. for 10 minutes.

i. After rapid shaking and centrifugation, the RNA concentration was measured on a microplate reader.

2. Synthesis of cDNA a. It is performed according to the instructions of the Rever Tra Ace qPCR RT Kit b. The adjustment was performed according to the RNA concentration, and 1 ng to 5 μg of total RNA were taken as a template. The reaction system was as follows:

| | |
|---|---|
| Deionized water | to 20 μl |
| 5 × RT Buffer | 4 μl |
| RT Enzyme Mix | 1 μl |
| Primer Mix | 1 ul |
| Template RNA | 0.5 pg to 1 μg |
| Total | 20 μl | c. The above was added to a nuclease-free PCR tube, an appropriate amount of total RNA template was added, and the deionized water was added to 20 ul. All operations were performed on ice.

d. Reaction conditions: 42° C., 15 minutes→85° C., 5 seconds→4° C., ∞, the cDNA was obtained after the reaction, and stored at −20° C. for later use.

3. Fluorescence Quantitative PCR Reaction a. The above cDNA was used as a template and GAPDH was used as an internal reference, the mRNA expression of M1/M2 macrophage-associated genes IL-6, TNF-α, CD80, CXCL9, CCL3, iNOS/Arg-1, CD206, IL-10, and CHI313 were determined by reference to the SYBR Green Realtime PCR Master MIX instructions.

b. A reaction solution was prepared according to the instructions of a Real-Time PCR kit:

| SYBR Green qPCR Master Mix | 10 μl |
|---|---|
| Upstream primer | 0.8 μl |
| Downstream primer | 0.8 μl |
| cDNA | 2 ul |
| Distilled water | 6.4 μl |
| Total | 20 μl | c. Reaction conditions: 95° C. 30 seconds→PCR cycle (X40 cycle): 95° C., 5 seconds; annealing, 55° C., 10 seconds; extension, 72° C., 15 seconds→preparation of melting curve statistical analysis d. GAPDH was used as an internal reference, an amplification curve and a melting curve of Real-time PCR were confirmed after the reaction was completed, and the Ct value of each template was detected. All samples were repeated 3 times, and the relative expression level of mRNA level in cells was calculated by a $2^{-\Delta\Delta Ct}$ method.

Figure 9:
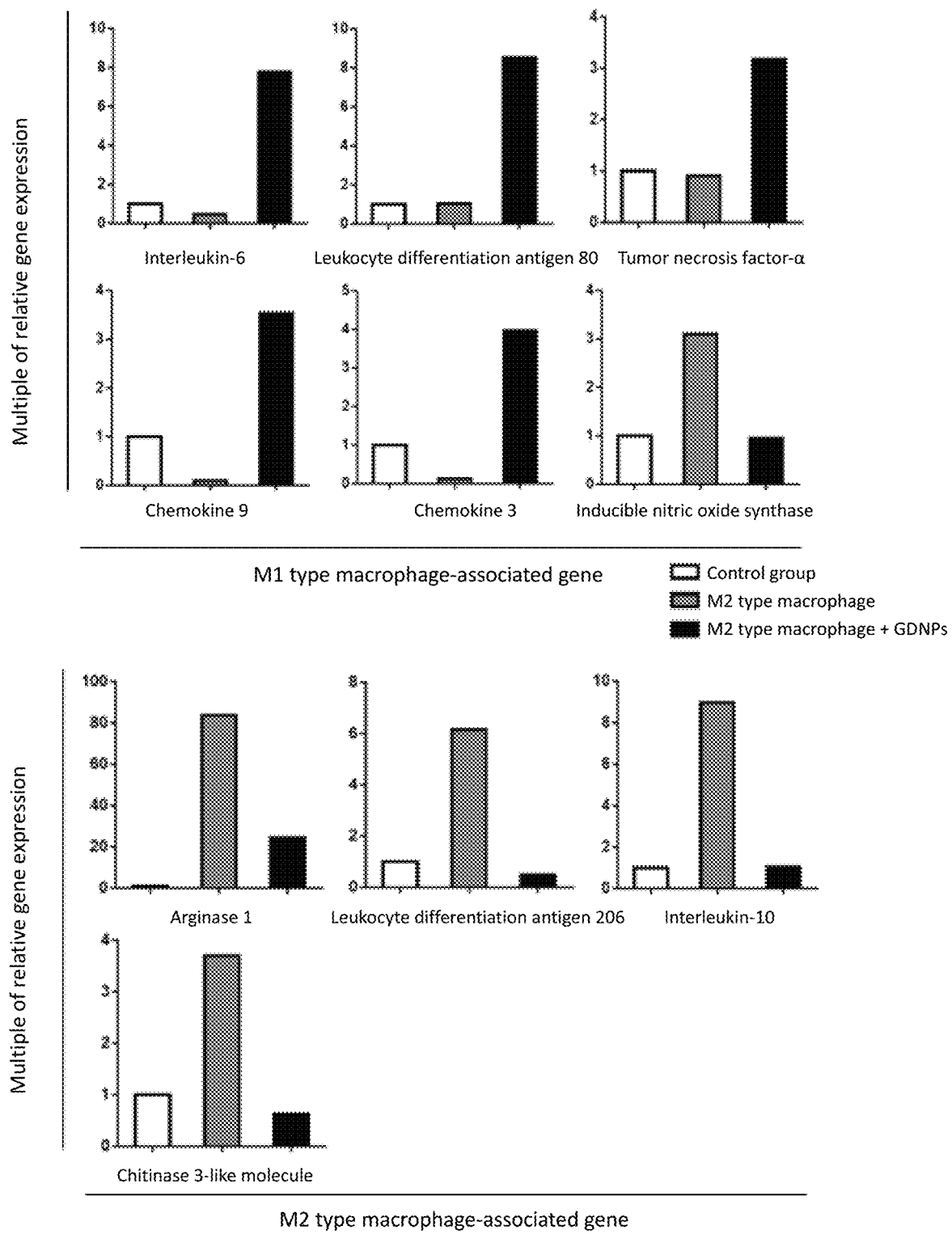
FIG. 9 shows that GDMPs down-regulate the transcription of M2 type macrophage-associated genes in vitro, while up-regulating the transcription of M1 type-associated genes.

As shown in FIG. 9, GDMPs can reduce the transcription level of M2 type macrophage-associated genes, while up-regulating the transcription level of M1 type cell-associated genes. From the results of transcription levels of M1/M2-associated genes, it is confirmed that GDMPs can polarize M2 type macrophages to M1 type.

Example 11: GDMPs Promote Secretion of TNF-α and IL-6 and Other Cytokines from M2 Type Macrophages In Vitro Detection of TNF-α and IL-6 in the culture supernatant of Example 1 (ELISA method) a. The capture antibody (anti-mouse TNF-α or IL-6) was diluted as required by the instructions, and coated in a 96-well plate at 100 ul/well at 4° C. overnight.

b. The plate was washed 3 times with PBST (PBS containing 0.5% Tween) for 3 minutes each time, and was then blocked with a 2% sheep serum blocking solution at 37° C. for 2 hours.

c. The plate was washed 3 times with PBST. A culture supernatant sample and a standard dilution were sequentially added to the blocked 96-well plate and incubated at 37° C. for 1 hour.

d. The plate was washed 5 times with PBST, and HRP-antimouse-TNF-α or IL-6 (1:10000) was added, and incubated at 37° C. for 1 hour.

e. The plate was washed 5 times with PBST, and a TMB coloring solution was added, and incubated at 37° C. for 15 minutes.

f. An $H_2SO_4$ stop solution was added and the OD value was measured at 450 nm.

g. The concentration of TNF-α or IL-6 was calculated based on the OD value.

Figure 10:
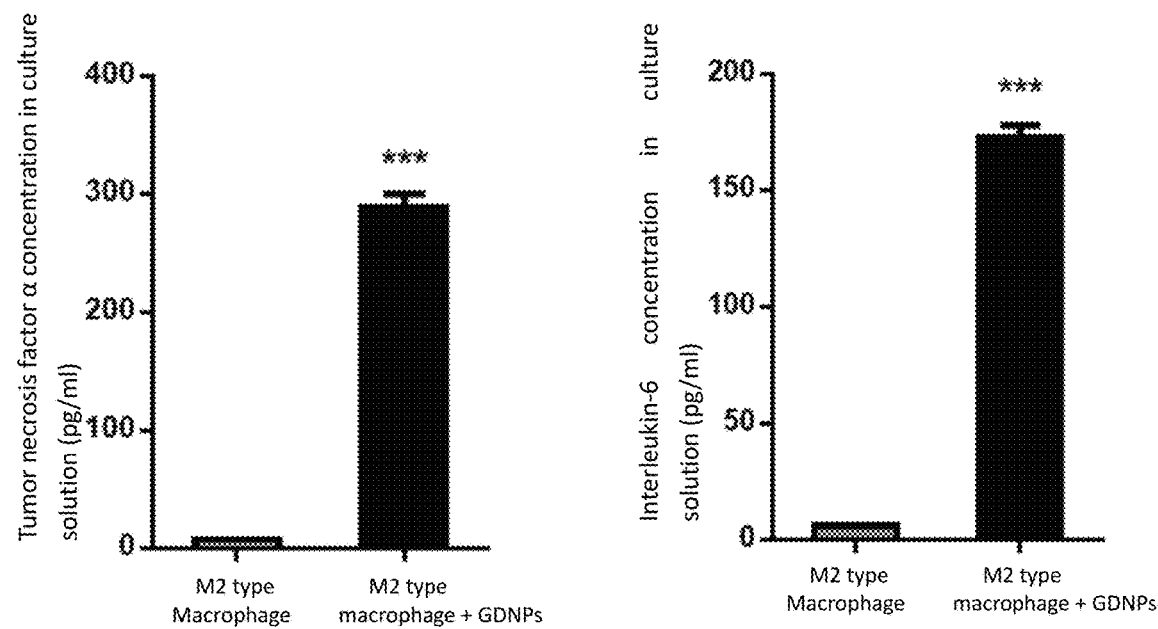
FIG. 10 shows that GDMPs promote the secretion of TNF-α, IL-6, and other M1 type cytokines from M2 type macrophage in vitro.

As shown in FIG. 10, GDMPs can promote M2 macrophages to secrete M1 type-associated cytokines (TNF-α and IL-6). From the perspective of secreted cytokines, it is confirmed that GDMPs can polarize M2 type macrophages to M1 type.

Figure 11:
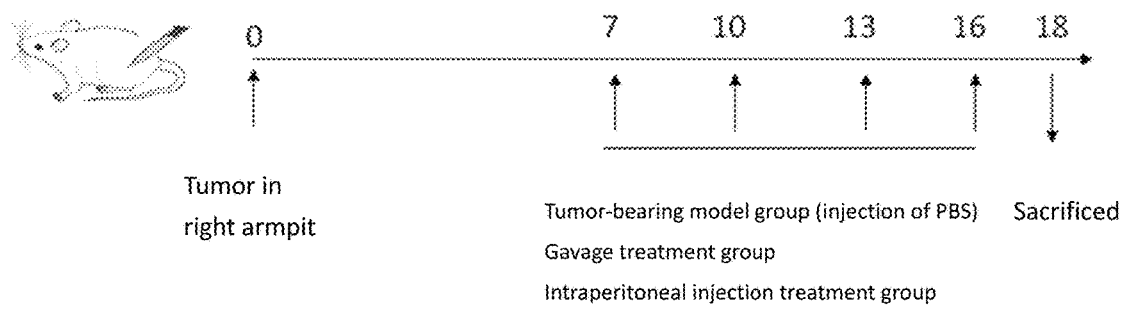
FIG. 11 is a schematic diagram of in vivo experiments of GDMPs for treating melanoma-bearing mice.
Figure 12:
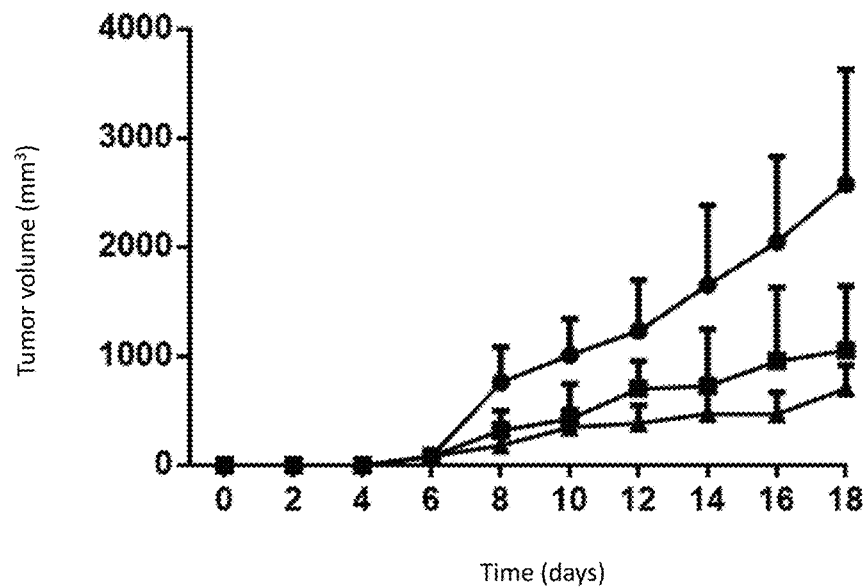
FIG. 12 shows the tumor growth curves in each group of mice during experiments.
Figure 13:
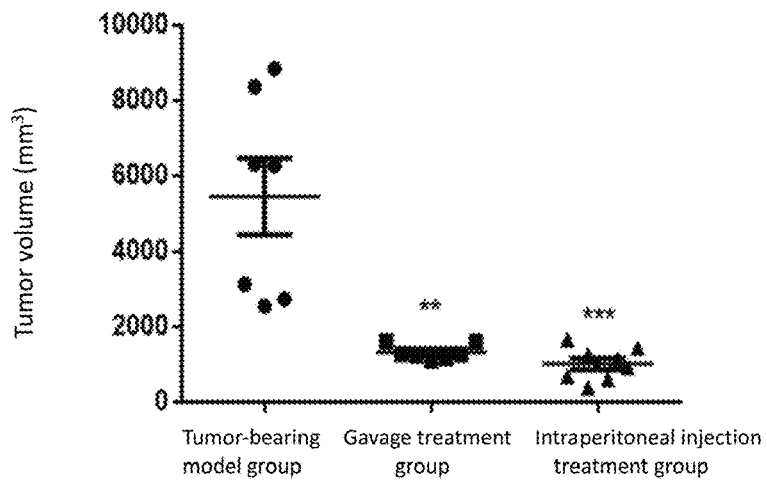
FIG. 13 shows the final tumor volume of each group of mice.
Figure 14:
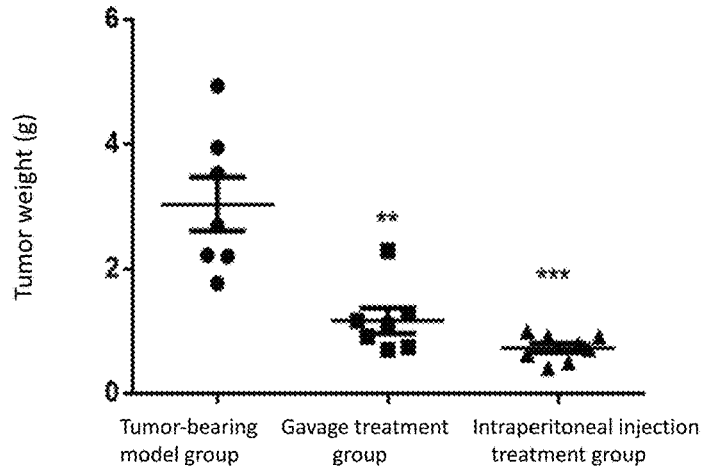
FIG. 14 shows the final tumor weight of each group of mice.
Figure 15:
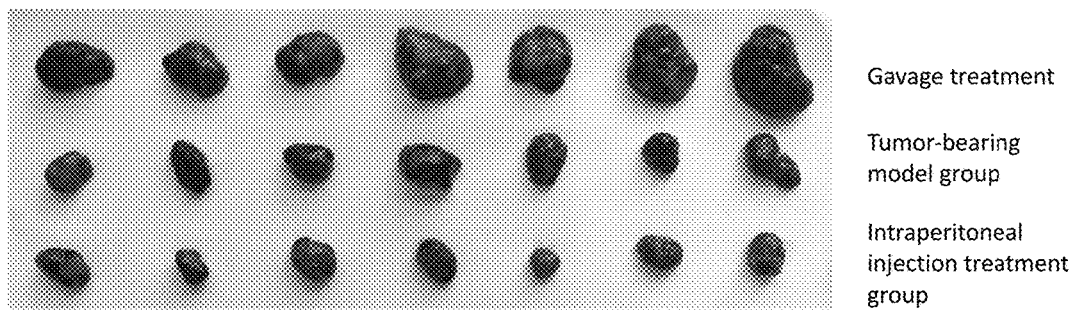
FIG. 15 shows the final tumor size of each group of mice.

Example 12: GDMPs Polarize M2 Type Macrophages in the Tumor Microenvironment to M1 Type In Vivo so as to Inhibit Tumor Growth a. Male C57/BL6 mice, 18-20 grams, were purchased from the Animal Experimental Center of Yangzhou University. Adaptive growth was performed for 1 week.

b. The mice were subcutaneously inoculated with mice melanoma cells-B16F10 ($2.5*10^5$ cells/mouse) into the right armpit and observed day by day.

c. 7 days after tumor inoculation, the average size of transplanted tumors reached 50 to 120 $mm^3$. The tumor-bearing mice were randomly divided into 3 groups: tumor-bearing model group (intraperitoneal injection of PBS), gavage treatment group (GDMPs 150 ug/mouse), and intraperitoneal injection treatment group (GDMPs 100 ug/mouse), and the treatment interval was 3 days (FIG. 11).

d. The growth status of each group of mice was observed day by day, and the body weight and tumor volume of the mice were measured every 2 days (tumor volume calculation=length*width²/2)

e. 11 days after treatment, the body weight was measured, then blood was sampled from the orbit, the mice were sacrificed by cervical dislocation, the tumor tissue was stripped to measure the volume and weight. The remaining major organs were separated and fixed with formaldehyde.

f. Part of the mice tumor tissue was taken, digested with collagenase for 30 minutes, ground, and filtered through a 200 mesh sieve to obtain a single cell suspension of tumor tissue, which was blocked with an Fc blocking agent (room temperature, 20 minutes).

g. Anti-mouse CD45, CD11b, CD206, CD80 and other monoclonal antibodies (room temperature, 30 minutes) were added respectively, and washed twice with PBS. The expression of the above molecules was identified by flow cytometry.

Figure 16:
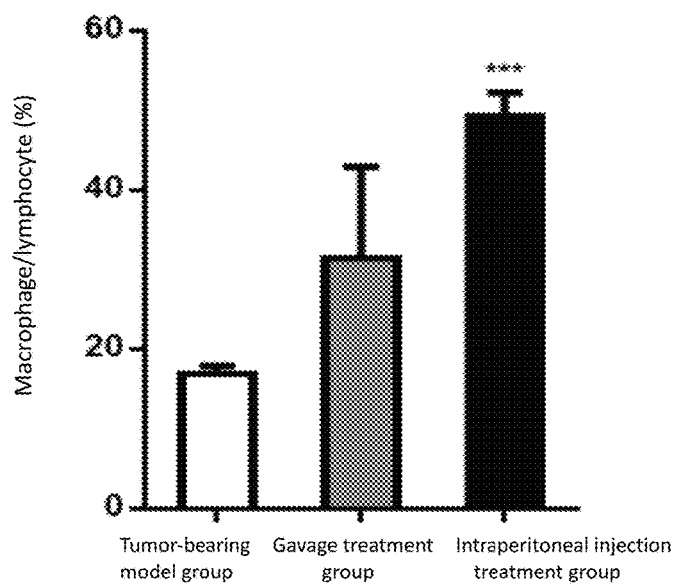
FIG. 16 shows the ratio of macrophages to lymphocytes in tumor tissues of each group of mice.
Figure 17:
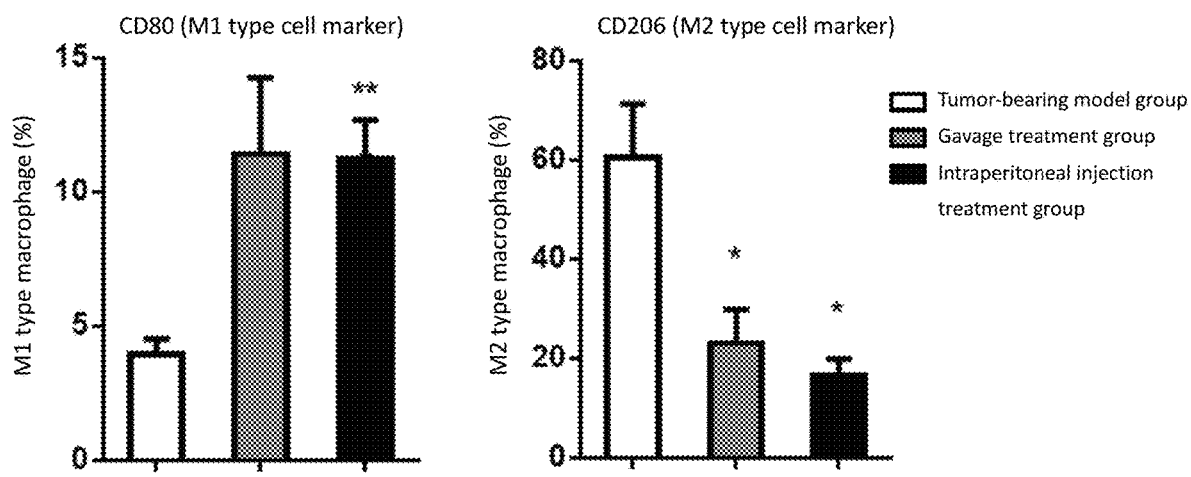
FIG. 17 shows the change in the number of M1/M2 type macrophages in tumor tissues of each group of mice.

The results show that both gavage treatment and intraperitoneal injection of GDMPs could inhibit the growth of mouse melanoma (FIGS. 12-15). By analyzing the proportion of lymphocytes in tumor tissues of each group of mice, it is found that in the tumor tissues of gavage treatment and intraperitoneal injection treatment groups of GDMPs, the proportion of macrophages in lymphocytes was significantly higher than that in the tumor-bearing model group (FIG. 16). At the same time, the proportion of M1/M2 macrophages in the tumor tissues of gavage treatment and intraperitoneal injection treatment groups is significantly higher (FIG. 17). These results suggest that GDMPs can effectively polarize M2 type macrophages in tumor tissues to M1 type in vivo, improve tumor microenvironment, and inhibit tumor growth.

What is claimed is:

1. A method for treating a disease by administering a ginseng-derived membranous microparticle to a subject in a need of treatment, wherein the disease is AIDS, active tuberculosis, oral *Candida albicans* infection, toxoplasma encephalopathy, tumor or Kaposi's sarcoma; wherein the ginseng-derived membranous microparticle has, a particle size ranging from 150 to 500 nm and a peak particle size of 280 to 350 nm, wherein the ginseng-derived membranous microparticle is prepared by following steps:

(1) squeezing fresh and washed ginseng by low-speed screw extrusion to obtain a slurry;

(2) filtering the slurry obtained in step (1) through a sieve to remove impurities and collecting a filtrate;

(3) sequentially subjecting the filtrate obtained in step (2) to low-speed, medium-speed, high-speed and ultra-speed centrifugation, discarding a precipitate after each centrifugation, and collecting a supernatant for the next centrifugation, wherein a precipitate is collected after the last centrifugation;

(4) resuspending the precipitate collected by the last centrifugation in step (3) with a buffer to form a mixture, then subjecting the mixture to ultra-speed centrifugation once, and collecting a precipitate; resuspending the precipitate with a buffer, then subjecting a mixture to high-speed centrifugation and collecting a supernatant; passing the supernatant through a sterilizing grade filter membrane to obtain the ginseng-derived membranous microparticle.

2. The method according to claim 1, wherein the ginseng-derived membranous microparticle is used as an immunopotentiator for activating monocyte-macrophages.

3. The method according to claim 2, wherein the method for activating monocyte-macrophages is promoting proliferation of the monocyte-macrophages and formation of colonies or up-regulating immunologically active molecules on the surface of monocyte-macrophages or promoting immunologically active cytokines secreted by monocyte-macrophages.

4. The method according to claim 1, wherein the ginseng-derived membranous microparticle is used for treating the tumor.

5. The method according to claim 4, wherein the method for treating tumor is depolarizing tumor-associated macrophages.

6. The method according to claim 4, wherein the method for depolarizing tumor-associated macrophages is: down-regulating surface marker molecules of M2 type macrophages, up-regulating surface marker molecules of M1 type macrophages, up-regulating cytokines secreted by the M1 type macrophages, and changing the proportion of the M1/M2 type macrophages in the tumor microenvironment, so as to kill tumors.

7. The method according to claim 6, wherein the M2 type macrophage-associated surface marker molecule is leukocyte differentiation antigen 206 (CD206); the M1 type macrophage-associated surface marker molecule is one or more of Toll-like receptor 2/4 (TLR2/4), leukocyte differentiation antigen 80 (CD80), leukocyte differentiation antigen 86 (CD86), and major histocompatibility complex 2 (MHC-II); the M2 type macrophage-associated gene is one or more of arginase 1 (Arg-1), leukocyte differentiation antigen 206, interleukin-10 (IL-10), and chitinase 3-like molecule (CHI313); the M1 type macrophage-associated gene is one or more of interleukin-6 (IL-6), tumor necrosis factor-$\alpha$ (TNF-$\alpha$), leukocyte differentiation antigen 80 (CD80), chemokine 9 (CXCL9), chemokine 3 (CCL3), inducible nitric oxide synthase (iNOS) and the like; the M1 type macrophage-associated immunologically active cytokine is one or more of tumor necrosis factor-$\alpha$ (TNF-$\alpha$) and interleukin-6 (IL-6).

* * * * *